(12) United States Patent
Schüle et al.

(10) Patent No.: US 8,293,494 B2
(45) Date of Patent: Oct. 23, 2012

(54) TRI-DEMETHYLATION-CAPABLE PROTEIN COMPLEX, METHOD OF ITS PREPARATION AND ITS USE

(75) Inventors: Roland Schüle, Weisweil (DE); Eric Metzger, Neuf-Brisach (FR); Melanie Wissmann, Freiburg (DE)

(73) Assignee: Universitatsklinikum Freiburg, Freiburg (DE)

( * ) Notice: Subject to any disclaimer, the term of this patent is extended or adjusted under 35 U.S.C. 154(b) by 0 days.

(21) Appl. No.: 12/524,472

(22) PCT Filed: Jan. 7, 2008

(86) PCT No.: PCT/EP2008/000055
§ 371 (c)(1),
(2), (4) Date: Oct. 29, 2009

(87) PCT Pub. No.: WO2008/089883
PCT Pub. Date: Jul. 31, 2008

(65) Prior Publication Data
US 2010/0081703 A1    Apr. 1, 2010

(30) Foreign Application Priority Data
Jan. 26, 2007    (EP) .................................... 07001721

(51) Int. Cl.
*C12Q 1/26*    (2006.01)
*C12Q 1/00*    (2006.01)
*G01N 33/53*    (2006.01)

(52) U.S. Cl. ................................ 435/25; 435/4; 435/7.1
(58) Field of Classification Search .................. None
See application file for complete search history.

(56) References Cited

U.S. PATENT DOCUMENTS

2009/0162945 A1* 6/2009 Cloos et al. .................... 436/501
2009/0203057 A1* 8/2009 Zhang et al. .................... 435/18

FOREIGN PATENT DOCUMENTS

EP    1 693 383    7/2005
EP    1 693 062    8/2006

OTHER PUBLICATIONS

Wissmann et al. Cooperative Demethylation by JMJD2C and LSD1 Promotes Androgen Receptor-Dependent Gene Expression; Nature Cell Biology, vol. 9, No. 3 (Mar. 2007) pp. 347-353.*
Cloos et al. The Putative Oncogene GASC1 Demethylates Tri- and Dimethylated Lysine 9 on Histone H3; Nature, vol. 442, No. 20 (Jul. 2006) pp. 307-311.*
Metzger et al. Histone Demethylation and Androgen-Dependent Transcription; Current Opinion in Genetics and Development, vol. 16 (2006) pp. 513-517.*
Tsukada et al. Histone Demethylation by a Family of JMJC Domain-Containing Proteins; Nature, vol. 439, No. 16 (Feb. 2006) pp. 811-816.*

Busso et al., "Construction of a set Gateway-based destination vectors for high-throughput cloning and expression screening in *Escherichia coli*," Analytical Biochemistry 343 (2005) 313-321.
Cloos et al., "The putative oncogene GASC1 demethylates tri- and dimethylated lysine 9 on histone H3," Nature, vol. 442, Jul. 20, 2006, pp. 307-311.
Gray et al., "Functional Characterization of JMJD2A, a Histone Deacetylase- and Retinoblastoma-binding Protein," The Journal of Biological Chemistry, vol. 280, No. 31, Aug. 5, 2005, pp. 28507-28518.
Fodor et al., "Jmjd2b anatagonizes H3K9 trimethylation at pericentric heterochromatin in mammalian cells," Genes Dev., 2006 20: 1557-1562.
Kang et al., "Involvement of Proteasome in the Dynamic Assembly of the Androgen Receptor Transcription Complex," the Journal of Biological Chemistry, vol. 277, No. 50, Dec. 13, 2002, pp. 48366-48371.
Klose et al., "The transcriptional repressor JHDM3A demethylates trimethyl histone H3 lysine 9 and lysine 36," Nature, vol. 442, Jul. 20, 2006, pp. 312-316.
Metzger et al., "LSD1 demethylates repressive histone marks to promote androgen-receptor-dependent transcription," Nature, vol. 437, Sep. 15, 2005, pp. 436-439.
Metzger et al., "A novel inducible transactivation domain in the androgen receptor: implications for PRK in prostate cancer," The EMBO Journal, vol. 22, No. 2, pp. 270-280, 2003.
Müller et al., "FHL2, a novel tissue-specific coactivator of the androgen receptor," The EMBO Journal, vol. 19, No. 3, pp. 359-369, 2000.
Müller et al., "The transcriptional coactivator FHL2 transmits Rho signals from the cell membrane into the nucleus," The EMBO Journal, vol. 21, No. 4, pp. 736-748, 2002.
O'Neill et al., "Nucleosome Arrays Inhibit Both Initiation and Elongation of Transcripts by Bacteriophage T7 RNA Polymerase," J. Mol. Biol. (1992) 223, pp. 67-78.
Rigaut et al., "A generic protein purification method for protein complex characterization and proteome exploration," Nature Biotechnology, vol. 17, Oct. 1999, pp. 1030-1032.
Rosenfeld et al., "Sensors and signals: a coactivator/corepressor/epigenetic code for integrating signal-dependent programs of transcriptional response," Genes Dev. 2006 20: pp. 1405-1428.
Shang et al., "Formation of the Androgen Receptor Transcription Complex," Molecular Cell, vol. 9, pp. 601-610, Mar. 2002.
Shi, X. et al., "ING2 PHD domain links histone H3 lysine 4 methylation to active gene repression," Nature, vol. 442, Jul. 6, 2006, pp. 96-99.
Shi, Y. et al., "Histone Demethylation Mediated by the Nuclear Amine Oxidase Homology LSD1," Cell, vol. 119, pp. 941-953, Dec. 29, 2004.
Strahl et al., "The language of covalent histone modifications," Nature, vol. 403, Jan. 6, 2000, pp. 41-45.
Trewick et al., "Methylation: lost in hydroxylation?" EMBO reports, vol. 6, No. 4, 2005, pp. 315-320.
Trojer et al., "Histone Lysine Demethylases and Their Impact on Epigenetics," Cell 125, Apr. 21, 2006, pp. 213-217.
Tsukada et al., "Histone demethylation by a family of JmjC domain-containing proteins," Nature, vol. 439, Feb. 16, 2006, pp. 811-816.

(Continued)

*Primary Examiner* — Jon P Weber
*Assistant Examiner* — Paul Martin
(74) *Attorney, Agent, or Firm* — K&L Gates LLP

(57) ABSTRACT

The invention relates to a multiple-specificity demethylase complex comprising a Jumonji C (JMJC) domain-containing enzyme, a process of its preparation and its use.

3 Claims, 14 Drawing Sheets

OTHER PUBLICATIONS

Figure 1:
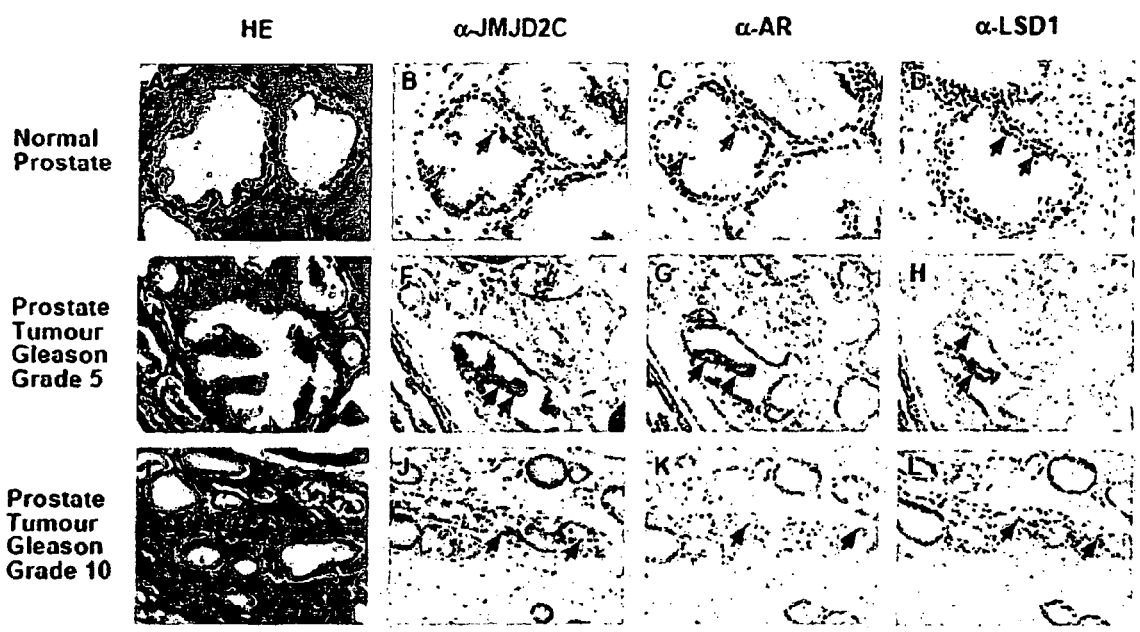
Figure 1:
Figure 1:
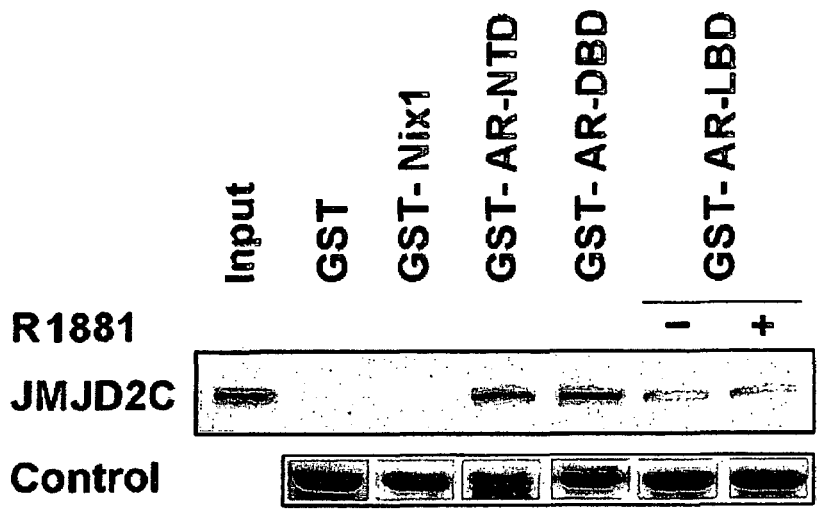
Figure 1:
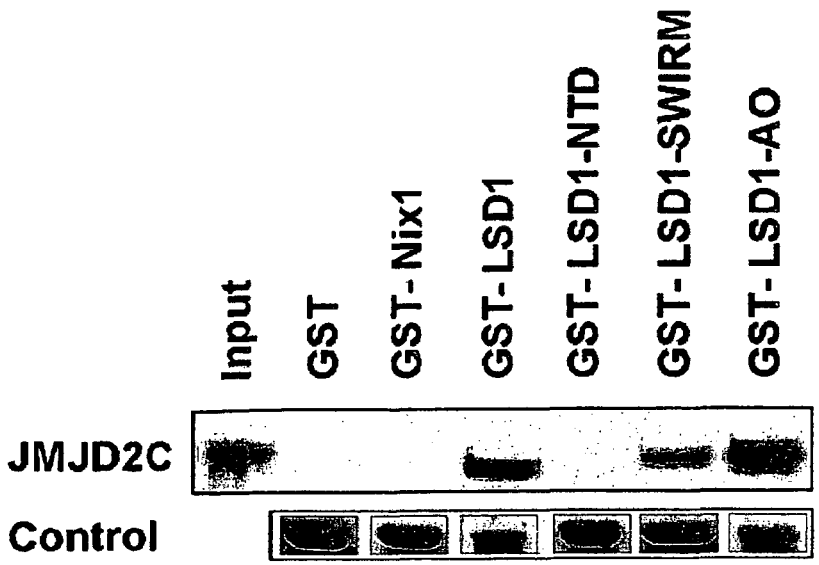

Whetstine et al., "Reversal of Histone Lysine Trimethylation by the JMJD2 Family of Histone Demethylases," Cell 125, pp. 467-481, May 5, 2006.

Wiznerowicz et al., "Conditional Suppression of Cellular Genes: Lentivirus Vector-Mediated Drug-Inducible RNA Interference," Journal of Virology, vol. 77, No. 16, Aug. 2003, pp. 8957-8961.

Wysocka et al., "A PHD finger of NURF couples histone H3 lysine 4 trimethylation with chromatin remodelling," Nature, vol. 442, Jul. 6, 2006, pp. 86-90.

Yamane et al., "JHDM2A, a JmjC-Containing H3K9 Demethylase, Facilitates Transcription Activation by Androgen Receptor," Cell 125, pp. 483-495, May 5, 2006.

* cited by examiner a b c d a c a b c d e a b c

TRI-DEMETHYLATION-CAPABLE PROTEIN COMPLEX, METHOD OF ITS PREPARATION AND ITS USE

CROSS-REFERENCE TO RELATED APPLICATIONS

This application claims the benefit of International Patent Application No. PCT/EP2008/000055 filed on Jan. 7, 2008, and European Patent Application No. 07001721.5 filed on Jan. 26, 2007, the disclosure of both of which are incorporated by reference in their entirety.

The present invention relates to a novel protein complex capable of demethylating histones. The invention also relates to a method of providing said protein complex and to the use of the complex in the medical field, in particular in the diagnosis and therapy of prostate cancer.

Histones, the essential regulators of the activity of genes in eukaryotic cells, are subject to a variety of post-translational modifications at their N-terminal tails, such as acetylation, phosphorylation, ubiquitination and methylation. Such reactions are controlled by specific chromatin-modifying enzymes (B. D. Strahl and C. D. Allis; "The language of covalent histone modifications"; Nature 403, 41-45 (2000)).

Lysine residues in histone tails may be mono-, di- or tri-methylated. The differently methylated lysine residues serve as docking sites for various effector proteins and chromatin modifiers. The results of such docking events are diverse physiological responses as, for example, transcriptional repression and activation (B. D. Strahl et al.; loc. cit.; X. Shi, et al.; ING2 PHD domain links histone H3 lysine 4 methylation to active gene repression. Nature 442, 96-99 (2006); J. Wysocka et al.; A PHD finger of NURF couples histone H3 lysine 4 trimethylation with chromatin remodelling. Nature 442, 86-90 (2006); M. G. Rosenfeld, V. V. Lunyak & C. K. Glass; Sensors and signals: a coactivator/corepressor/epigenetic code for integrating signal-dependent programs of transcriptional response. Genes Dev. 20, 1405-1428 (2006)).

Changes in levels of histone methylation have been associated with cancer and have been shown to predict the clinical outcome of prostate tumor (P. Kahl, L. Gullotti, L. C. Heukamp, S. Wolf, N. Friedrichs, R. Vorreuther, G. Solleder, P. J. Bastian, J. Ellinger, E. Metzger, R. Schüle, R. Buettner; Androgen receptor coactivators lysine-specific histone demethylase 1 and four and a half LIM domain protein 2 predict risk of prostate cancer recurrence. Cancer Res. 66, 11341-11347 (2006).

Steps of a methylation and demethylation are universally used to post-translationally modify histones for the regulation of gene activity. For example, Lysine-specific demethylase 1 (LSD1), a nuclear amine oxidase homolog recently identified, functions as a histone lysine demethylase (Y. Shi et al.; "Histone demethylation mediated by the nuclear amine oxidase homolog LSD1"; Cell 119, 941-953 (2004); E. Metzger et al.; "LSD1 demethylates repressive histone marks to promote androgen receptor-dependent transcription"; Nature 437, 436-439 (2005)). Recombinant LSD1 is highly specific for histone H3, mono- and dimethylated at lysine 4 and lysine 9 (H3-K4me, H3-K4me2, H3-K9me, and H3-K9me2), while other known methylation sites of H3 and H4 histones are no substrates for this protein (Shi et al.; loc. cit., Metzger et al.; loc. cit.).

Jumonji C (JMJC) domain-containing hydroxylases are further candidate demethylases and demonstrate that histone methylation is reversible and dynamically regulated (J. R. Whetstine et al.; "Reversal of histone lysine trimethylation by the JMJD2 family of histone demethylases"; Cell 125, 467-481 (2006); Z. Chen et al.; "Structural Insights into histone demethylation by JMJD2 family members"; Cell 125, 691-702 (2006)).

It was shown previously that LSD1 interacts with the androgen receptor (AR) and promotes ligand-dependent transcription of AR target genes resulting in enhanced prostate tumor cell growth (EP-A 1 693 062 and 1 693 383). Ligand-induced activation of target genes demands the removal of the repressive histone marks mono-, di- and trimethyl histone H3 at lysine 9 (H3K9). In in vitro and in vivo experiments, it could be confirmed that LSD1 is capable of removing only H3-K9me and H3-K9me2, but not H3K9me3 (Metzger et al. (2005), loc. cit.). Thus, ligand-induced demethylation of trimethyl H3K9 and subsequent AR target gene activation requires an as yet undiscovered specific histone tridemethylase.

JMJC domain-containing enzyme proteins, and in particular the JMJD2 gene family, were recently identified, and structure-demethylating reactivity relationships were elucidated. A summary is found in Z. Chen et al., loc. cit. One member of this protein family containing, in addition to the JMJC domain, further domains (JMJN domain, PHD domains, Tudor domains), is JMJD2C, which was found to have histone demethylase activity. JMJD2C was described to be upregulated in squamous cell carcinomas (Z. Q. Yang et al., "Identification of a novel gene, GASC1, within an amplicon at 9p23-24 frequently detected in esophageal cancer cell lines"; Cancer Res. 60, 4735-4739 (2000)). It is reported that JMJD2C targets H3K9me3 for demethylation (J. R. Whetstine et al. (2006), loc. cit.).

It was the object of the present invention to provide enzyme proteins having histone demethylating activity, particularly having broad-specificity demethylating activity and, more particularly, having tridemethylating activity. Furthermore, it was an object of the present invention to provide enzyme proteins having demethylating activity, more particularly having tri-demethylating activity and targeting specific genes, for example the androgen receptor (AR). Moreover, it was an object of the present invention to provide a process of obtaining and isolating such enzyme proteins. A further object of the present invention is to demonstrate such enzyme proteins for use in the medical field, particularly in the inhibition of prostate cancer, for screening purposes and for preventing the expression of AR, PR and GR target genes by RNAi mediated knockdown of JMJD2C or chemical inhibition of JMJD2C activity.

Hence, the invention relates to a multiple-specificity demethylase complex comprising a Jumonji C (JMJC) domain-containing enzyme.

The invention also relates to the multiple-specificity demethylase complex as described above for use in the medical field.

The invention further relates to a process for preparing a multiple-specificity demethylase complex comprising a Jumonji C (JMJC) domain-containing enzyme by associating said Jumonji C (JMJC) domain-containing enzyme with a substrate on which the enzyme may act, optionally while supplying, and/or in the presence of, further enzyme complex components.

The invention also relates to the multiple-specificity demethylase complex as specified in more detail below for a use in the medical field.

Moreover, the invention relates to a process for removing methyl substituents from a histone, particularly from lysine residues of a histone, said process comprising the step of contacting at least one histone with an effective amount of a multiple-specificity demethylase complex comprising a Jumonji C (JMJC) domain-containing enzyme.

Furthermore, the invention also relates to a process for modulating, preferably promoting, the transcriptional activity of the AR, comprising the steps of: using cells or a system expressing endogenous AR or transfecting a sample of the AR with an effective amount of a multiple-specificity demethylase complex described in detail below and observing the transcriptional activity change.

Furthermore, the invention also relates to a process for modulating, preferably promoting, the transcriptional activity of the progesterone receptor (PR), comprising the steps of: using cells or a system expressing endogenous PR or transfecting a sample of the PR with an effective amount of a multiple-specificity demethylase complex described in detail below and observing the transcriptional activity change.

Furthermore, the invention also relates to a process for modulating, preferably promoting, the transcriptional activity of the glucocorticoid receptor (GR), comprising the steps of: using cells or a system expressing endogenous GR or transfecting a sample of the GR with an effective amount of a multiple-specificity demethylase complex described in detail below and observing the transcriptional activity change.

Moreover, the invention relates to a process for stimulating a ligand-dependent AR activity exerted by either of the demethylating enzymes LSD1 and JMJC domain-containing enzyme, preferably LSD1 and an enzyme of the JMJD2 family, more preferably LSD1 and the enzyme JMJD2C, comprising the step of employing a demethylase complex comprising LSD1 and a JMJC domain-containing enzyme, preferably LSD1 and an enzyme of the JMJD2 family, more preferably LSD1 and the enzyme JMJD2C.

Further, the invention relates to a process for controlling an androgen-dependent gene regulation and cell proliferation, said process comprising the step of controlling the demethylase activity of one or more of the components of a multiple-specificity complex described in detail below.

Further, the invention relates to a process for the activation of AR target genes by the step of allowing a co-operative action of components of a multiple-specificity complex described in detail below with the aim of a specific demethylation of the repressive histone mark trimethyl H3K9.

Moreover, the invention relates to a process for the prevention and therapy of prostate cancer through an inhibition of an androgen-dependent proliferation of prostate tumor cells by the step of modulating, preferably inhibiting, the demethylating action of at least one component of a multiple-specificity demethylase complex described in detail below.

In addition, the invention relates to a process for suppressing the expression of at least one demethylase, preferably the expression of more than one demethylase, more preferably the expression of more than one demethylase of the multiple-specificity demethylase complex of any of the claims 1 to 3, by exposing a biological system controlled by said at least one demethylase, preferably by more than one demethylase, more preferably by of more than one demethylase of the multiple-specificity demethylase complex as described in detail below, to at least one RNAi, thereby knocking down said at least one demethylase.

Moreover, the invention also relates to a process for modulating a target gene expression and gene-induced cell proliferation by suppressing the expression of at least one enzyme relevant for such modulation by using at least one RNAi, preferably by suppressing the expression of at least one demethylase, preferably by suppressing the expression of more than one demethylase, more preferably by suppressing the expression of more than one demethylase of the multiple-specificity demethylase complex as described in detail below, by using at least one RNAi.

Further details and embodiments of the invention can be seen from the Figures which show the following:

FIG. 1 JMJD2C co-localises and interacts with both, AR and LSD1. a, Immunohistochemical staining of JMJD2C, AR, and LSD1 in human normal and tumour prostate. JMJD2C (B, F, J), AR (C, G, K), and LSD1 (D, H, L) immunoreactivity is detected in the secretory epithelium of normal prostate (B, C, D, arrows) and prostate carcinoma cells (F, G, H, J, K, L arrows). Hematoxilin-eosin (HE) stained sections are shown in A, E, and I. All sections were taken from the same radical prostatectomy specimen. Magnification: ×250. b, JMJD2C interacts with AR (left panel) and LSD1 (right panel) in vivo. Extracts from mouse prostate were immunoprecipitated with either α-JMJD2C, α-LSD1, α-cyclin A antibodies or rabbit IgG. Western blots were decorated with α-AR, α-JMJD2C, or α-LSD1 antibodies as indicated.

JMJD2C, LSD1, and, AR are present in a single protein complex. 293 cells were transfected with expression plasmids for V5-JMJD2C, Flag-AR, and either TAP-LSD1 or TAP as indicated. Protein complexes were immobilised on IgG, sepharose, released from IgG sepharose by TEV protease cleavage of the TAP tag, followed by immunoprecipitation of Flag-tagged AR with α-Flag antibody. The presence of LSD1 and JMJD2C in association with AR was confirmed by Western blotting with α-LSD1, α-AR, and, α-V5 antibodies, respectively. Ten percent of the extract used for immunoprecipitation was loaded as input.

c, d GST pull-down assays were performed with labelled JMJD2C and the bacterially expressed and purified GST-AR fusion proteins, GST-LSD1 or fusion proteins thereof. GST and GST-Nix1 proteins were used as control. (NTD; N-terminal domain, DBD; DNA-binding domain, LBD; ligand-binding domain, AO; amine oxidase domain). Coomassie blue staining shows the amounts of GST fusion proteins used.

Figure 2:
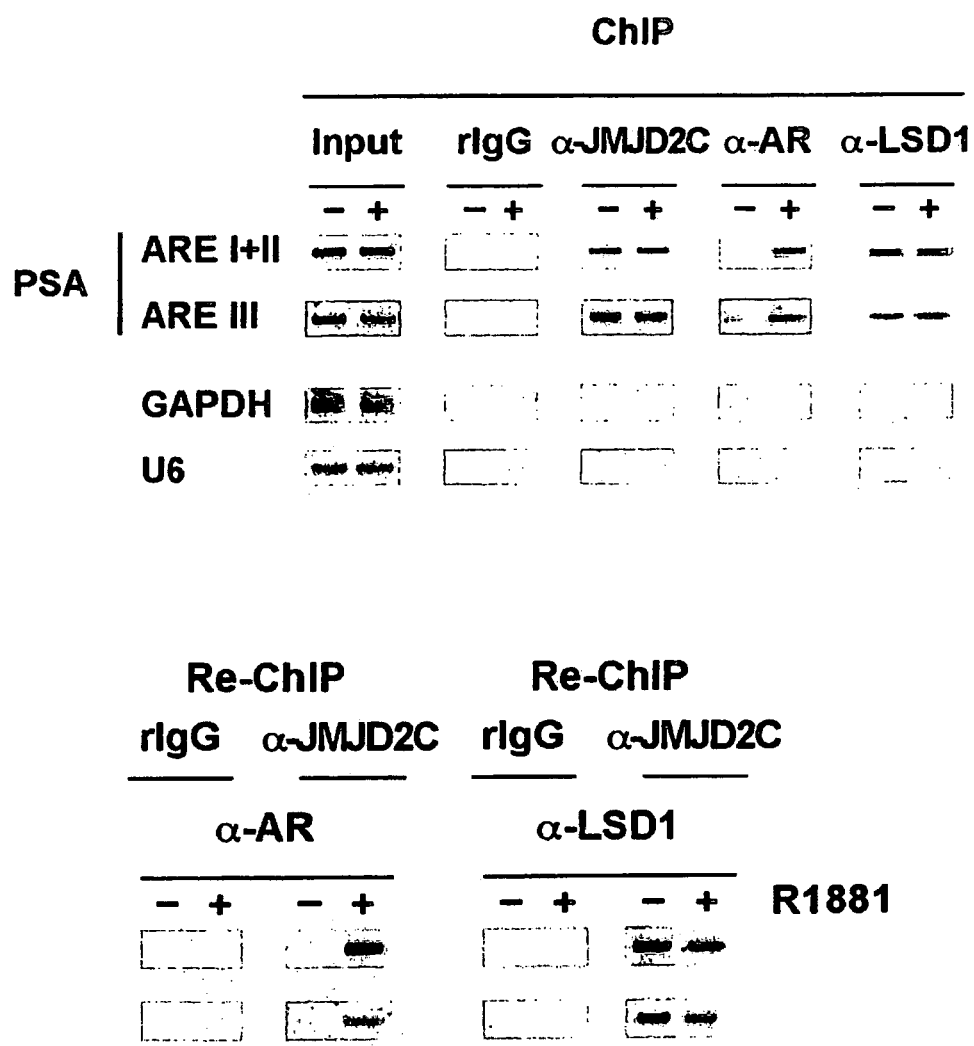

FIG. 2 JMJD2C interacts with chromatin and demethylates H3K9. LNCaP cells were incubated with or without the AR agonist R1881 (a, b), and transfected with stealth RNAi (b). ChIP or Re-ChIP was performed with the indicated antibodies. The precipitated chromatin was amplified by PCR using primers flanking the promoter region (ARE I+II) and the enhancer region (ARE III) of the PSA gene, the promoter region (ARE) of the KLK2 gene, or the promoters of the unrelated GAPDH and U6 genes. Western blot analysis (b, lower right panel) verified the specific siRNA-mediated knockdown of JMJD2C. c, Core histones or nucleosomes from HeLa cells were incubated with recombinant JMJD2C (aa 12-349) or mutant JMJD2C H190A (aa 12-349). Western blots were decorated with the indicated antibodies against α-mono-, α-di-, or α-trimethyl H3K9.

Figure 3:
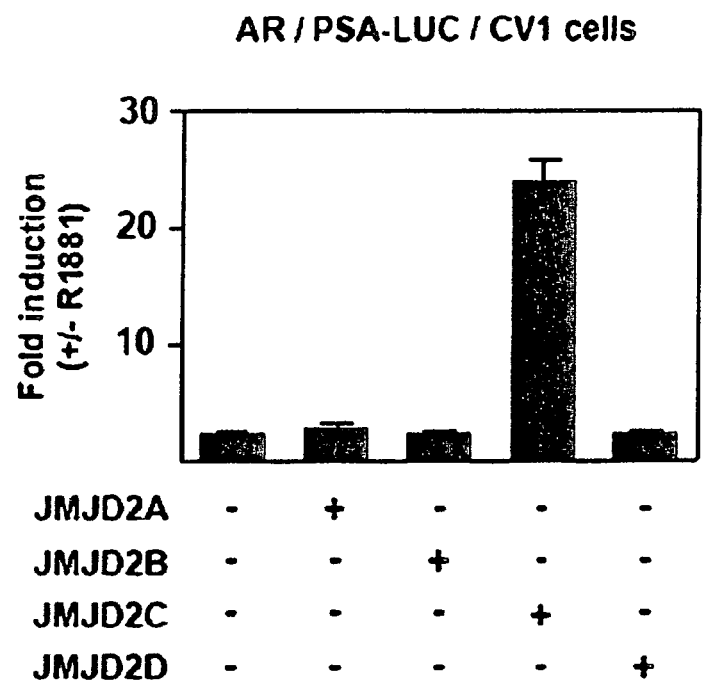
Figure 3:
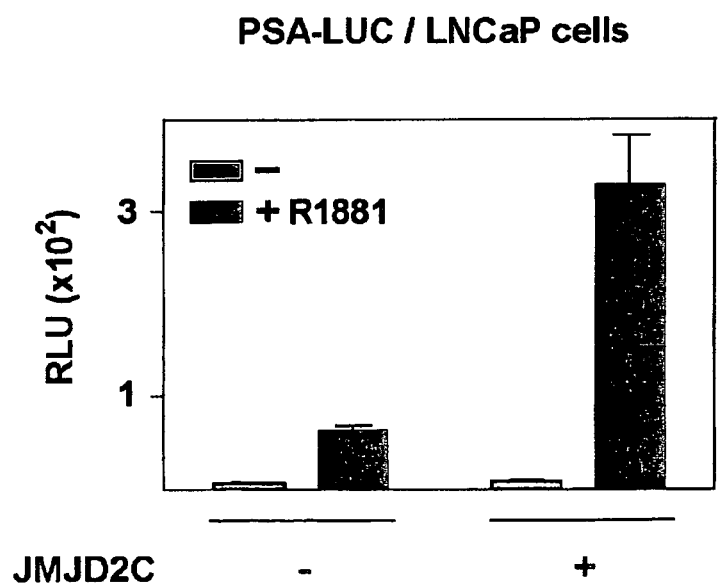
Figure 3:
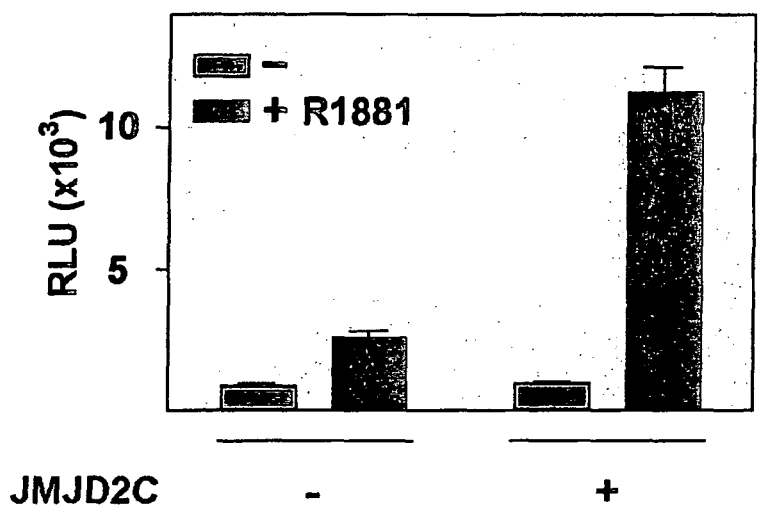
Figure 3:
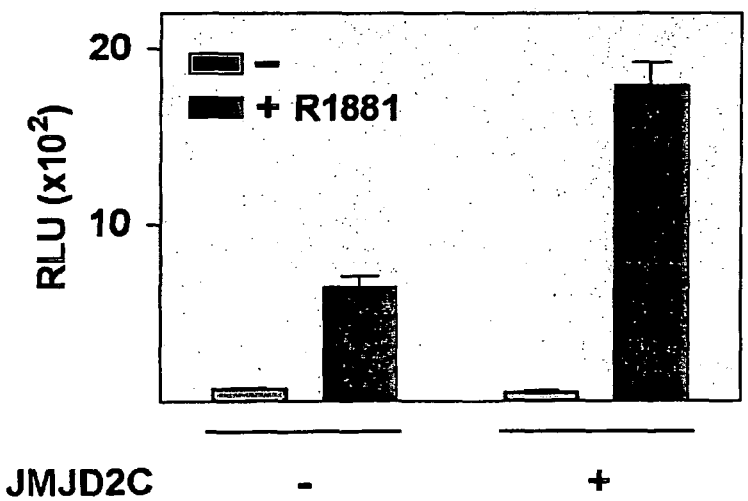
Figure 3:
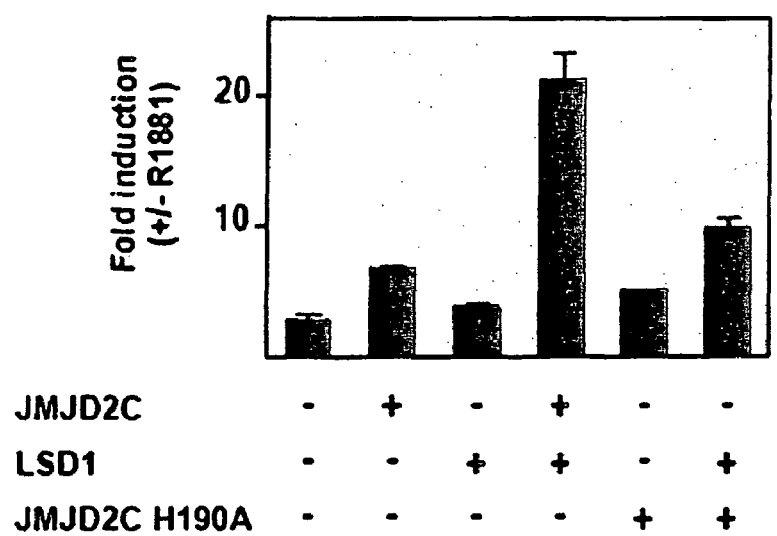

FIG. 3 JMJD2C controls AR-induced transcriptional activity. CV1 (a, c, d, e), or LNCaP (b) cells were transfected with AR-dependent reporters in the presence or absence of R1881. CV1 cells were co-transfected with AR expression plasmid (a, c, d, e). JMJD2C but not the other JMJD2 family members JMJD2A, JMJD2B, or JMJD2D (a) controls AR-induced transcriptional activity on different natural AR-regulated promoters and cell lines (a, b, c, d). JMJD2C also regulates the transcriptional activity of other nuclear receptor family members.

Limited amounts (200 ng) of JMJD2C, JMJD2C H190A, or LSD1 were tested for co-operative stimulation of AR-dependent reporter activity (e). Bars represent mean +SD ($n \geq 5$).

Figure 4:
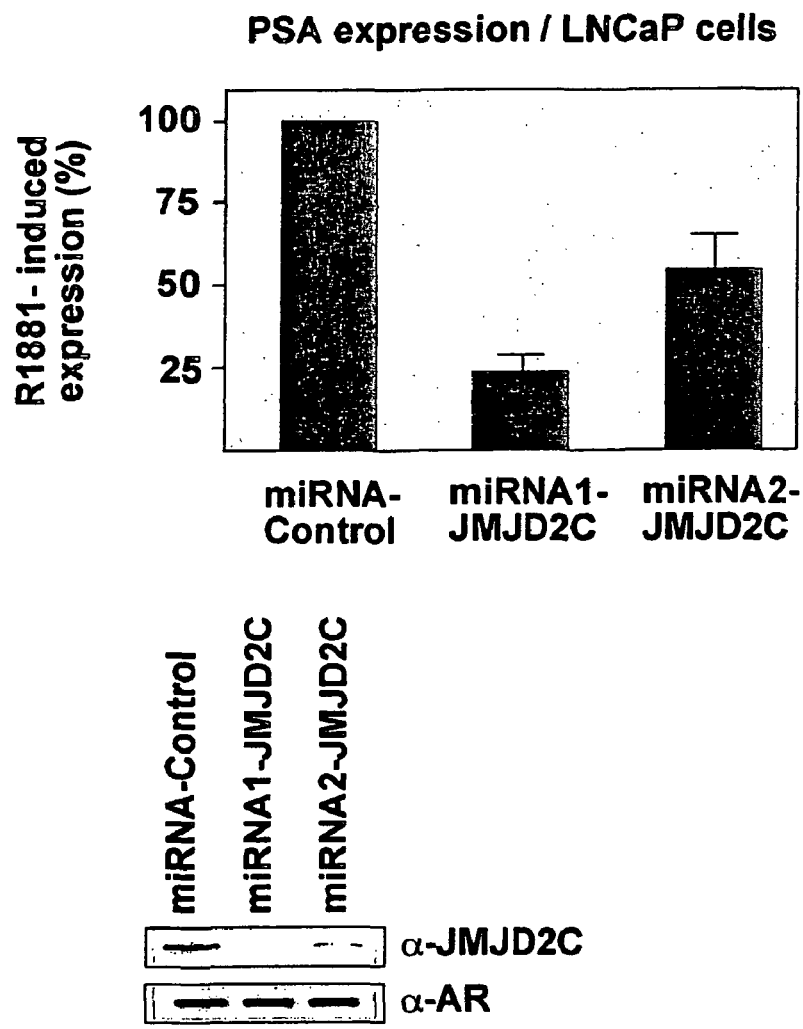
Figure 4:
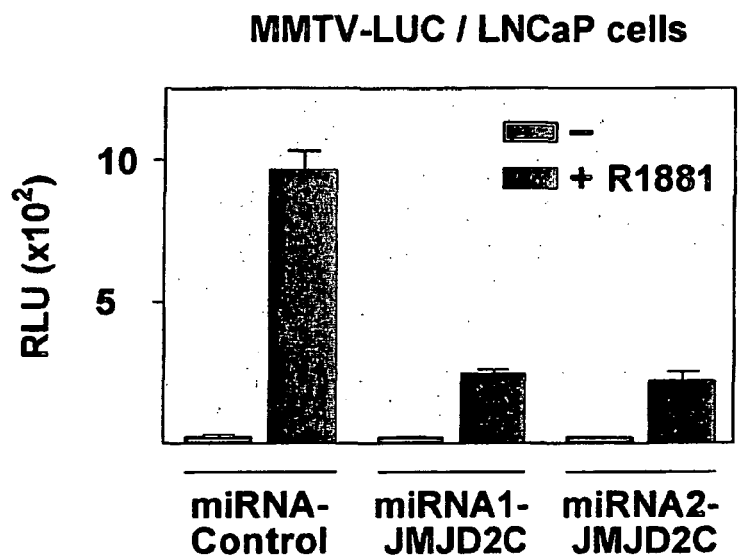
Figure 4:
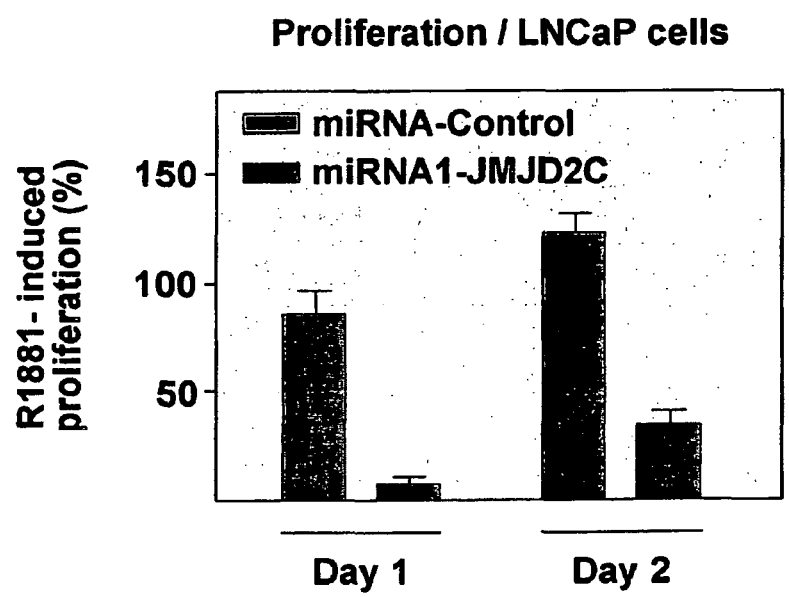

FIG. 4 JMJD2C knockdown blocks AR-induced transcriptional activity and tumour cell proliferation. In LNCaP cells, miRNA-mediated JMJD2C knockdown reduces expression of the endogenous PSA gene (a, upper panel), AR-dependent reporter activity (b), and R1881-induced cell proliferation (c). Knockdown of JMJD2C was verified by Western blot analysis (a, lower panel) using α-JMJD2C or α-AR antibodies. Bars represent mean +SD (n≧4).

Confocal laser scanning microscopy shows the sub-cellular localisation of endogenous JMJD2C and AR in human LNCaP prostate tumour cells. AR (red) co-localises with JMJD2C (green) in the nucleus upon addition of the AR agonist R1881.

Figure 5:
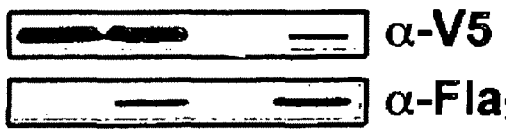
Figure 5:
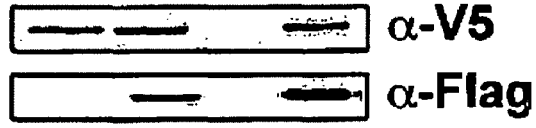

FIG. 5: JMJD2C interacts with AR (upper panel) and LSD1 (lower panel) in vivo. 293 cells were transfected with expression plasmids for V5-JMJD2C and either Flag-AR or Flag (upper panel), or V5-JMJD2C and either Flag-LSD1 or Flag (lower panel) in the presence of $10^{-10}$ M R1881 as indicated. Extracts were immunoprecipitated with α-Flag (M2, Sigma) antibody. Five percent of the extract used for immunoprecipitation was loaded as input Western blots were decorated with α-V5 (Invitrogen; 1:5000) or α-Flag antibody (1:2500).

Association of bacterially expressed AR and JMJD2C in vitro. Western blot analysis using α-JMJD2C antibody show that bacterially expressed and purified MBP-JMJD2C interacts with bacterially expressed and purified GST-AR fusion proteins but not with the GST and GST-Nix1 control proteins. (NTD; N-terminal domain, DBD, DNA-binding domain, LBD, ligand-binding domain, MBP; maltose-binding protein). 1 percent of the extract used for pull-down was loaded as input.

Full-length AR interacts with JMJD2C in vitro. MBP pull-down assays were performed with labelled full-length AR (ARwt) and the bacterially expressed and purified MBP-JMJD2C fusion protein. MBP protein was used as control. 1 percent of the extract used for pull-down was loaded as input.

Association of bacterially expressed LSD1 and JMJD2C in vitro. Western blot analysis using α-JMJD2C antibody show that bacterially expressed and purified MBP-JMJD2C interacts with bacterially expressed and purified GST-LSD1 and fusion proteins thereof, but not with the GST and GST-Nix1 control proteins. (NTD; N-terminal domain, AO; amine oxidase). 5 percent of the extract used for pull-down was loaded as input.

JMJD2C interacts with chromatin at ARE I, ARE II, and ARE III of the PSA gene. LNCaP cells were incubated with or without the AR agonist R1881. ChIP experiments were performed with α-JMJD2C antibody. The precipitated chromatin was amplified by PCR using primers flanking the promoter region (ARE I (-237/-122) and ARE II (-458/-330)) and the enhancer region (ARE III (-4213/-4043)). Primer sequences are as follows:

```
ARE I (-237/-122):
5'-TTTGTCCCCTAGATGAAGTCTCC-3'
(SEQ ID NO: 1)
and

5'-CCCACACCCAGAGCTGTGGAAGG-3',
(SEQ ID NO: 2)

ARE II (-458/-330):
5'-GCCAAGACATCTATTTCAGGAGC-3'
(SEQ ID NO: 3)
and

5'-CCTTTGCACTCCAAGACCCAGT-3',
(SEQ ID NO: 4)

ARE III (-4213/-4043):
5'-TGCTCAGCCTTTGTCTCTGATGA-3'
(SEQ ID NO: 5)
and

5'-ATATCTCTCTCAGATCCAGGCTT-3'.
(SEQ ID NO: 6)
```

The siRNA mediated knockdown of JMJD2C is specific. 293 cells were transfected with siRNA against JMJD2C or control siRNA and expression plasmids for human Flag-JMJD2A, Flag-JMJD2B, Flag-JMJD2C, or Flag-JMJD2D. Western blot was decorated with α-Flag antibody (1:2500).

Figure 6:
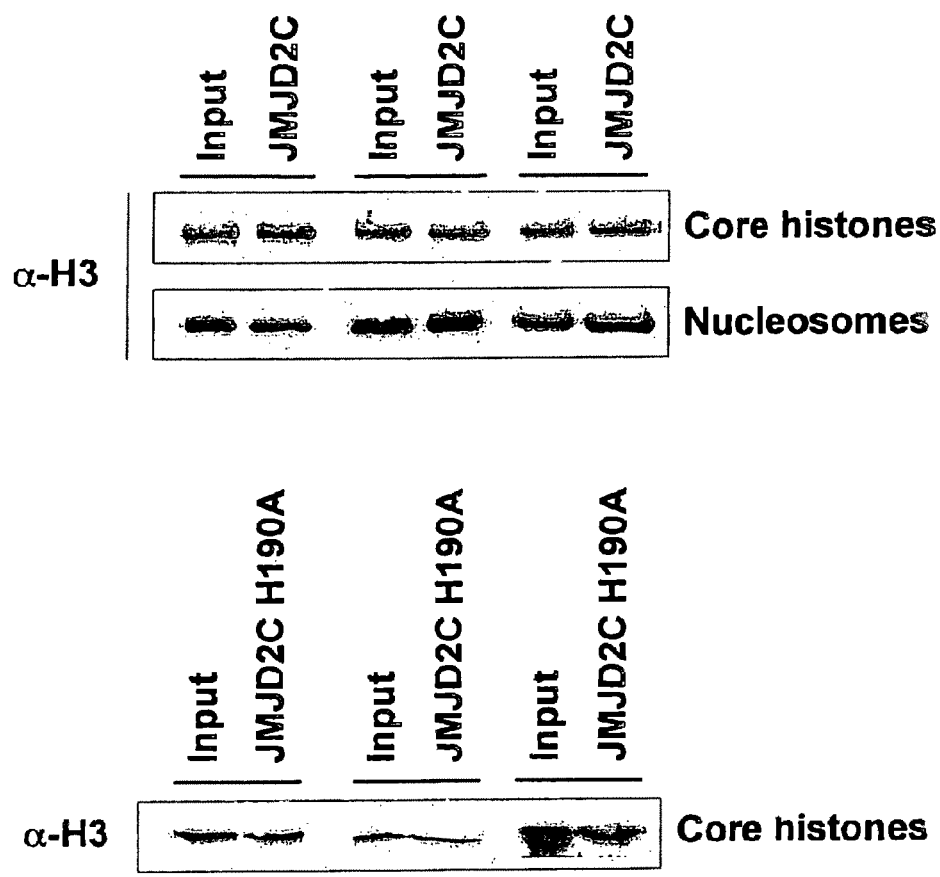

FIG. 6: The integrity of core histones and nucleosomes is maintained during the demethylation assay. Core histones or nucleosomes from HeLa cells were incubated with recombinant JMJD2C (aa 12-349) or mutant JMJD2C H190A (aa 12-349). Western blots were decorated with α-H3 antibody.

Figure 7A:
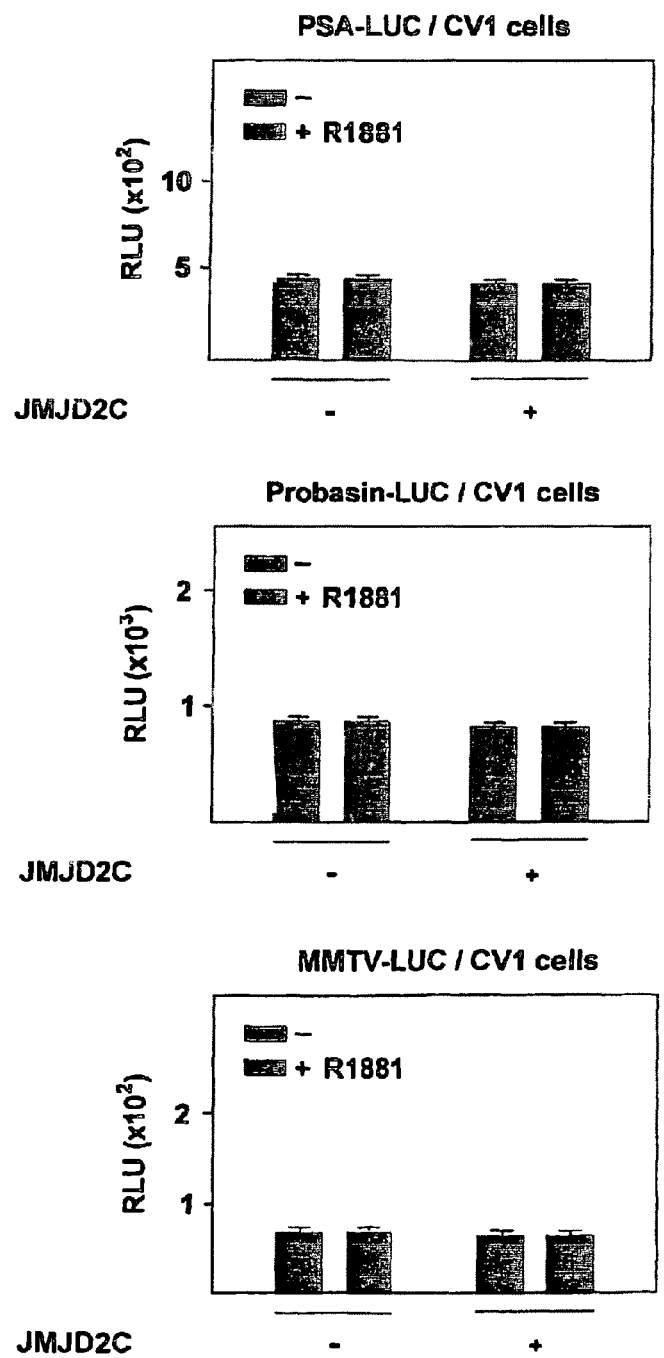

FIG. 7a: In the absence of AR, JMJD2C does not induce activation of the AR-regulated reporters PSA-LUC, Probasin-LUC, and MMTV-LUC. CV1 cells were transfected as indicated in the presence or absence of $10^{-10}$ M R1881. Bars represent mean +SD (n≧5).

Figure 7B:
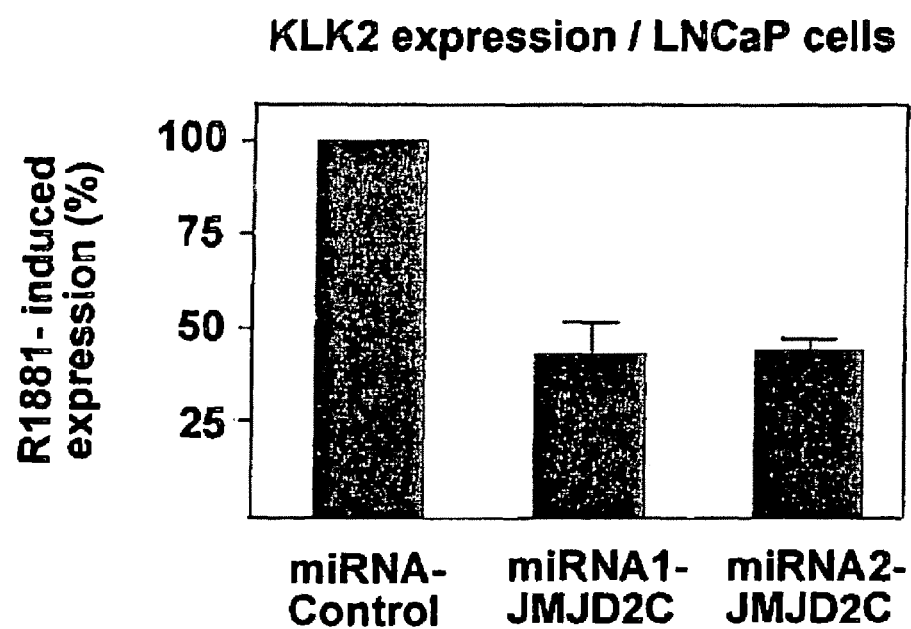

FIG. 7b: miRNA-mediated JMJD2C knockdown reduces ligand-dependent expression of the endogenous KLK2 gene in LNCaP cells. Bars represent mean +SD (n≧4).

Knockdown of either LSD1 or JMJD2C does not influence each other's association with chromatin. LNCaP cells were incubated in the presence or absence of the AR agonist R1881 and transfected with the indicated RNAi. ChIP was performed with the indicated antibodies. The precipitated chromatin was amplified by PCR using primers flanking the promoter region (ARE I+II). Western blot analysis verified the specific siRNA-mediated knockdown.

JMJD2B does not interact with LSD1 in vivo. JMJD2B is expressed in LNCaP Cells but does neither associate with the PSA promoter nor assemble with LSD1 in vivo. Western blots were decorated with the indicated antibodies (α-JMJD2A, Abcam; 1:1000, JMJD2B, Aviva Systems Biology; 1:500, and JMJD2D, Aviva Systems Biology; 1:1000) Extracts from LNCaP cells were immunoprecipitated with either α-LSD1, α-cyclin A antibodies or rabbit IgG. LNCaP cells were incubated with or without the AR agonist R1881 and ChIP experiments were performed with the indicated antibodies. The precipitated chromatin was amplified by PCR using primers flanking the promoter region (ARE I+II) of the PSA gene.

JMJD2C does not interact with JHDM2A. 293 cells were transfected with expression plasmids for GFP-JHDM2A and either Flag-JMJD2C or Flag. Extracts were immunoprecipitated with α-Flag antibody. Twenty percent of the extract used for immunoprecipitation was loaded as input. Western blots were decorated with α-GFP (Santa Cruz; 1:500) or α-Flag antibody (1:2500).

The α-JMJD2C antibody specifically recognizes JMJD2C. 293 cells were transfected with expression plasmids for Flag-JMJD2A, V5-JMJD2B, Flag-JMJD2C or Flag-JMJD2D. Western blots were decorated with α-JMJD2C, α-Flag (1:2500) or α-V5 antibody (1:5000).

Expression levels of JMJD2C and LSD1 in CV1 cells. CV1 cells were either mock transfected or transfected with 200 ng or 400 ng expression plasmids for Flag-JMJD2C or Flag-LSD1, respectively. Western blots were decorated with α-JMJD2C or α-LSD1 antibody.

The invention is now explained in more detail by referring to the Figures. However, when referring to the Figures, preferred embodiments of the invention are shown which are given for exemplary and explanatory purposes, only. The invention is by no means restricted to these preferred embodiments.

The invention relates to a multiple-specificity demethylase complex as claimed in claim 1.

The term "multiple-specificity", as used in the present specification and claims, refers to the fact that, due to a content, of the complex, of more than one enzyme having demethylase activity, demethylating activities of different specificities can be covered. Particularly, more than one demethylase contained in said complex and, specifically, assembled on chromatin to remove methyl groups from mono-, di- and trimethylated H3K9 may have different specificities so that a co-operative removal of methyl groups (co-operative demethylation) can be achieved by the present invention.

The term "demethylase complex", as used in the present specification and claims, refers to an assembly of more than one demethylase, i.e. enzymes catalyzing a demethylation reaction, in close association or close spatial relationship, allowing a co-ordinate action, i.e. demethylating action, of said enzymes or demethylase complex. In a preferred embodiment of the invention, said more than one, for example two, three or even more, preferably two, demethylases form a closely assembled arrangement of components having demethylating enzymatic activity. In a particularly preferred embodiment, said arrangement or complex may include further components described in detail below.

The multiple-specificity demethylase complex of the invention comprises a Jumonji C domain-containing enzyme (JMJC domain-containing enzyme). JMJC domain-containing enzymes were described in the prior art (Y. I. Tsukada et al.; Histone demethylation by a family of JMJC domain-containing proteins; Nature 435, 811-816 (2005); J. R. Whetstine et al.; Reversal of Histone Lysine Trimethylation by the JMJD2 Family of Histone Demethylases; Cell 125, 467-481; (2006); P. A. Cloos et al.; The putative oncogene GASC1 demethylates tri- and dimethylated lysine 9 on histone H3; Nature 442, 307-311 (2006); K. Yamane et al.; JHDM2A, a JMJC-Containing H3K9 Demethylase, Facilitates Transcription Activation by Androgen Receptor; Cell 125, 483-495 (2006); S. C. Trewick, P. J. McLaughlin & R. C. Allshire; Methylation: lost in hydroxylation? EMBO Rep. 6, 315-320 (2005); B. D. Fodor et al.; JMJD2B antagonizes H3K9 trimethylation at pericentric heterochromatin in mammalian cells; Genes Dev. 20, 1557-1562 (2006); P. Trojer & D. Reinberg; Histone lysine demethylases and their impact on epigenetics; Cell 125, 213-217 (2006)), and their demethylating activities are known in general.

In a preferred embodiment of the invention, the demethylase complex comprises a member of the JMJD2 enzyme family, which enzyme family was recently described to be characterized by the common structure feature, inter alia, of the JMJC domain within each molecule of the family (Z. Chen (2006), loc. cit.). It is even more preferred in accordance with the invention that the demethylase complex comprises the enzyme JMJD2C as the JMJC domain-containing demethylase enzyme.

In accordance with the present invention, the demethylase complex may contain further components, which a skilled person in this field may select in accordance with their utility for the present purpose, i.e. to exert a demethylating enzymatic action. In a preferred embodiment which results into a surprising demethylating enzymatic activity, the demethylase complex may comprise at least one further enzyme, more preferably one further enzyme capable of effecting demethylating activity, i.e. at least one further demethylase, more preferably one further demethylase. In view of the known demethylating character, a number of other enzymes may be selected without any restriction. It is, however, even more preferred due to the surprising demethylating effect (which is in detail described below) that the demethylase complex of the invention advantageously comprises lysine-specific demethylase 1 (LSD1) as the enzyme effecting demethylating activity. As will be seen from the further description of the invention, JMJD2C and LSD1 are assembled in a demethylase complex of the invention and exhibit a very effective demethylation action.

A further preferred embodiment of the invention is directed to a demethylation complex which further comprises a target gene. Said target gene may be selected from a group consisting of a large number of target genes and, specifically, may be the androgen receptor (AR) or the progesterone receptor (PR) or the glucocorticoid receptor (GR). Such a complex may be found in cases where, for example and preferred, but not restricting, JMJD2C, AR (or PR or GR) and LSD1 (only for AR, not for PR or GR) are co-localized in a cell, for example (for AR) in a prostate cell or prostate carcinoma cell.

The invention also relates to a process for preparing a multiple-specificity demethylase complex, said complex comprising a Jumonji C (JMJC) domain-containing enzyme. The process comprises the step of associating said Jumonji C (JMJC) domain-containing enzyme with a substrate on which the enzyme may act. In accordance with the invention, it is optional to supply further enzyme complex components and/or to conduct the associating step in the presence of further enzyme complex components.

The terms "associating" and "associating step", as used in the present specification and claims, means the step of bringing two or more components of the complex into close spatial relationship (as defined above) for a subsequent co-operative action of said components.

In a preferred embodiment of the process of the invention, a member of the JMJD2 enzyme family is employed as the JMJC domain-containing enzyme. In view of the excellent demethylating action, it is even more preferred that JMJD2C is employed as the Jumonji C (JMJC) domain-containing enzyme.

Further preferred embodiments of the invention by which particularly effective enzyme complexes can be prepared, are directed to a preparation process for the complex, wherein at least one further enzyme capable of effecting demethylating activity is supplied or is present, preferably wherein lysine-specific demethylase 1 (LSD1) is supplied or is present.

In a further preferred embodiment of the invention, a target gene, preferably the androgen receptor (AR) or the progesterone receptor (PR) or the glucocorticoid receptor (GR), is present in the demethylase complex.

In accordance with the present invention, the new multi-specificity demethylase complex may be used for different purposes, but it is preferred that the complex is used in the medical field, where it may have advantageous effects in connection with a number of useful applications which are described end exemplified below.

One application example which is preferred in accordance with the invention due to the broad application which may be derived particularly in the biochemical and medical fields is a process for removing methyl substituents from a histone. As already addressed above, the demethylation of the N-terminal tails of histones is one of the common posttranslational modification reactions. Particularly the lysine residues of histones are demethylated. The process of the invention comprises the step of contacting at least one histone with an effective amount of a multiple-specificity demethylase complex comprising a Jumonji C (JMJC) domain-containing demethylase enzyme. As will be described below in detail in connection with the experiments supporting the present invention, an effective demethylation reaction can be achieved by said process step. The process may comprise the contact of one histone, practically (but not restricted) at its lysine residues, with the complex comprising at least one demethylating enzyme, or more than one histone may be contacted with the demethylating enzyme or enzymes; it is preferred that one histone is contacted with the complex comprising at least one demethylating enzyme.

In a preferred embodiment of the process of the invention, said at least one histone is contacted with a demethylase complex comprising a member of the JMJD2 enzyme family as the JMJC domain-containing enzyme, and even more preferably, said at least one histone is contacted with a demethylase complex comprising JMJD2C as the Jumonji C domain-containing enzyme.

In view of a multiple specificity demethylating action, it is even more preferable in the present invention that said at least one histone is contacted with a demethylase complex further comprising at least one further enzyme capable of effecting demethylating activity, preferably comprising lysine-specific demethylase 1 (LSD1).

In another preferred embodiment of the process described above, said at least one histone is contacted with a demethylase complex further comprising a target gene, preferably further comprising the androgen receptor (AR), progesterone receptor (PR) or glucocorticoid receptor (GR).

As will be seen from the detailed description and the examples below, the invention finds its application in a number of fields, particular in the medical and biochemical field. The examples shown below are, however, not restricting, and a skilled person will be able to apply the invention to further fields which are covered by the claims which follow.

In accordance with the invention, there is provided a process for modulating the transcriptional activity of the AR. It is preferred that the modulation process is a promoting process. Said process comprises the steps of: using cells or a system expressing endogenous AR or transfecting a sample of the androgen receptor (AR) with an effective amount of a multiple-specificity demethylase complex described in detail above and observing the transcriptional activity change.

In accordance with the invention, there is provided a process for modulating the transcriptional activity of the progesterone receptor (PR). It is preferred that the modulation process is a promoting process. Said process comprises the steps of: using cells or a system expressing endogenous PR or transfecting a sample of the progesterone receptor (PR) with an effective amount of a multiple-specificity demethylase complex described in detail above and observing the transcriptional activity change.

In accordance with the invention, there is provided a process for modulating the transcriptional activity of the glucocorticoid receptor (GR). It is preferred that the modulation process is a promoting process. Said process comprises the steps of: using cells or a system expressing endogenous GR or transfecting a sample of the glucocorticoid receptor (GR) with an effective amount of a multiple-specificity demethylase complex described in detail above and observing the transcriptional activity change.

In a further preferred embodiment of the invention, there is provided a process for stimulating a ligand-dependent AR activity exerted by either of the demethylating enzymes LSD1 and JMJC domain-containing enzyme, preferably by either of LSD1 and an enzyme of the JMJD2 family, more preferably by either of LSD1 and the enzyme JMJD2C, comprising the step of employing a demethylase complex comprising LSD1 and a JMJC domain-containing enzyme, preferably LSD1 and an enzyme of the JMJD2 family, more preferably LSD1 and the enzyme JMJD2C.

Another preferred embodiment of the invention is directed to a process for controlling generally a signaling substance-dependent, preferably—and exemplarily—an androgen-, progestin-, or glucocorticoid-dependent gene regulation and cell proliferation, said process comprising the step of controlling the demethylase activity of one or more of the components of a multiple-specificity complex as described in detail above. The signaling substance may be any substance occurring in an organism and being capable of sending biochemical signals to another part of said organism having any physiological effect, e.g. hormones.

Preferred in accordance with the invention is also a process for the activation of androgen receptor (AR), GR or PR target genes by the step of allowing a co-operative action of components of a multiple-specificity complex as described in detail above with the aim of a specific demethylation of the repressive histone mark trimethyl H3K9.

Another preferred process of the invention having a high value in the medical field is a process for the prevention and therapy of prostate cancer through an inhibition of an androgen-dependent proliferation of prostate tumor cells by the step of modulating, preferably inhibiting, the demethylating action of at least one component of a multiple-specificity demethylase complex as described above in detail. In said process, the demethylating action of one demethylase complex component may be modulated, preferably inhibited, or the demethylating action of more than one (two, three etc.) demethylase complex component may be modulated, preferably inhibited. Particularly preferred is the modulation or inhibition of two components of the demethylase complex, even more preferred the modulation or inhibition of the demethylating action of JMJD2C and LSD1 as components of the demethylase complex.

Further embodiments of the invention are directed to a process for searching for and/or screening substances controlling (for example: blocking) the demethylase activity of a multiple-specificity demethylase complex as described above in detail, said process comprising the steps of: contacting at least one substance to be searched for or to be screened with a reaction system comprising said multiple-specificity demethylase complex and at least one compound capable of being demethylated enzymatically by at least one component of said complex and evaluating the influence of said at least one substance to be searched for or to be screened on the enzymatic demethylation. In view of the fact that an improvement of the control or blocking action of the demethylase activity of the multi-specificity demethylase complex was already attempted for a long time, achieving such an improvement is surprising and has a great value in connection with finding new controlling (or blocking) substances for the future. In connection with the above process, the invention also provides for a kit for such a searching or screening method allowing an easy practice thereof. The kit comprises the reaction system addressed, i.e. said multiple-specificity demethylase complex and at least one compound capable of being demethylated enzymatically by at least one component of said complex.

The invention also relates to a process for searching for and/or screening substances controlling (for example: blocking) the interaction of LSD1 and a JMJC domain-containing enzyme, preferably the interaction of LSD1 and a member of the JMJD2 enzyme family, more preferably the interaction between LSD1 and JMJD2C, said process comprising the steps of: contacting at least one substance to be searched for or to be screened with a reaction system comprising LSD1 and a JMJC domain-containing enzyme, preferably comprising LSD1 and a member of the JMJD2 enzyme family, more preferably comprising LSD1 and JMJD2C, and at least one compound capable of being demethylated enzymatically by at least one of said demethylases, and evaluating the influence of said at least one substance to be searched for or screened on the enzymatic demethylation. With respect to the kit provided for conducting this process of the invention, the above disclosure is applied here mutatis mutandis.

The invention also relates to a process for searching for and/or screening substances controlling (for example: blocking the modulating activity of a multiple-specificity demethylase complex as described above in detail on the AR, GR or PR, said process comprising the steps of: contacting at least one substance to be searched for or to be screened with a reaction system comprising said multiple-specificity demethylase complex and the AR, and evaluating the influence of said at least one substance to be searched for or screened on the enzymatic demethylation. Also in this case, a kit is provided, and the above information is applied to this embodiment mutatis mutandis.

In a further preferred embodiment of the invention, the influence of demethylases in general, and of the multiple-specificity demethylase complex of the invention in particular, and more preferably of a JMJC domain-containing enzyme, and even more preferably of the enzyme JMJC2C, optionally in the presence of other enzymes having demethylase capability, as for example LSD1, on biological systems was elucidated by a process for suppressing the expression of at least one demethylase, preferably the expression of more than one demethylase, more preferably the expression of more than one demethylase of the multiple-specificity demethylase complex as described in detail above, by exposing a biological system controlled by said at least one demethylase, preferably by more than one demethylase, more preferably by of more than one demethylase of the multiple-specificity demethylase complex as described in detail above, to at least one RNAi, thereby knocking down said at least one demethylase. While the knockdown of LSD1 could already be shown earlier (E. Metzger et al., loc. cit), the present invention could establish, by experiments described below, the knockdown of JMJC domain-containing enzymes as, for example, JMJD2C. In accordance with the invention, the biological system, wherein said suppression of the expression of demethylase(s) may be achieved may be any cell and may preferably be a cell (for example, but not restricting, a human cell) where the expression of target genes, the cell proliferation etc. is to be modulated by the (optionally reversible) histone methylation/demethylation. Examples of such cells which, however, do not restrict the invention, are prostate cells, more specifically prostate tumour cells. By such a demethylase knockdown, the expression of target genes as, for example, the expression of the androgen receptor (AR), GR or PR target genes may be modulated. As a consequence, the cell proliferation, e.g. the androgen-induced tumour cell proliferation, may be slowed down or even stopped.

Hence, the invention also relates, in another preferred embodiment, to a process for modulating a target gene expression and gene-induced cell proliferation by suppressing the expression of at least one enzyme relevant for such modulation by using at least one RNAi, preferably by suppressing the expression of at least one demethylase, preferably by suppressing the expression of more than one demethylase, more preferably by suppressing the expression of more than one demethylase of the multiple-specificity demethylase complex as described in detail above, by using at least one RNAi. The latter process may be relevant particularly in preventing tumor cell proliferation, and one field of application may be the prevention and therapy of prostate tumors, without being restricted to this field.

Further details of the invention are now described specifically and just to give examples of the preferred embodiments of the invention; no restriction of the invention should be derived from the following detailed description.

Using a candidate approach[11] to discover such a tridemethylase we identified JMJD2C[5,6]. To investigate whether JMJD2C co-localises with AR we used immunohistochemical analyses of prostate and prostate tumour biopsies on tissue microarrays. As shown in FIG. 1a, JMJD2C is detected in the epithelium of normal prostate and in prostate carcinoma cells. These cells also express LSD1 demonstrating that JMJD2C not only co-localises with AR but also with the demethylase LSD1 (FIG. 1a). Furthermore, as shown in co-immunoprecipitation assays endogenous JMJD2C and AR specifically associate in prostate (FIG. 1b). Importantly, JMJD2C also interacts with LSD1 in vivo (FIG. 1b; FIG. 5). To demonstrate that all three proteins exist in a single protein complex we applied a TAP-based co-purification strategy. 293 cells were transfected with Flag-AR, V5-JMJD2C, and either TAP-LSD1 or TAP. The TAP-LSD1 associated protein complexes were immobilised on IgG sepharose and the presence of both AR and JMJD2C in the immobilised LSD1 complexes was verified by Western blot analysis. AR and JMJD2C do not co-purify in the presence of the TAP control demonstrating specific association of AR and JMJD2C with TAP-LSD1. LSD1 associated complexes were released from IgG sepharose by TEV protease cleavage of the TAP-tag followed by immunoprecipitation of Flag-tagged AR with α-Flag antibody. The specific association of JMJD2C and LSD1 with AR in a single protein complex was verified by Western blot analysis. We applied the TAP-based co-purification strategy because the moderate expression levels of the endogenous proteins would only have allowed a limited number of purification steps. Therefore, using common methodology such as gel filtration/density gradient centrifugation would have left us with the uncertainty that two very similar yet still distinct complexes, e.g. one containing AR and JMJD2C, the other containing AR and LSD1, could have been co-purified.

We further show in GST pull-down analyses that full-length JMJD2C directly interacts with the N-terminal domain (NTD), the DNA-binding domain (DBD), and the ligand-binding domain (LBD) of AR (FIG. 1c). JMJD2C does not associate with the controls GST or GST-Nix1, thus demonstrating specificity of interaction with AR in vitro. In addition, JMJD2C interacts with full-length LSD1. The association with JMJD2C is mediated by the centrally located: SWIRM domain, and the C-terminal amine oxidase (AO) domain that harbours the demethylase activity[2] (FIG. 1d). Taken together, our data show that JMJD2C, AR, and LSD1 are not only co-expressed in prostate but also interact in vitro and in vivo.

To determine whether JMJD2C associates with chromatin in vivo, LNCaP human prostate tumour cells were subjected to chromatin immunoprecipitation (ChIP) in the presence or absence of the AR agonist R1881. JMJD2C associates with the androgen response elements (ARE I+II and ARE III) located in the promoter and enhancer of the Prostate Specific Antigen (PSA) gene in a ligand-independent manner (FIG. 2a). This association is specific since the promoters of the unrelated GAPDH and U6 genes are not enriched. AR occupies the AREs of the PSA gene only in the presence of ligand (FIG. 2a and ref[3]). To demonstrate that JMJD2C and AR form a complex, on the PSA promoter, R1881-treated LNCaP cells were subjected to sequential chromatin immunoprecipitation (Re-ChIP), first with α-AR antibody and then with α-JMJD2C antibody. Importantly, both ARE-containing regions were specifically enriched, demonstrating that JMJD2C and ligand-bound AR form a complex on chromatin (FIG. 2a). As shown previously, LSD1 associates with chromatin both in the presence and absence of ligand (FIG. 2a and ref[3]). Notably, Re-ChIP experiments demonstrate that JMJD2C and LSD1 assemble together on the AREs of the PSA promoter (FIG. 2a). In summary, these data suggest the assembly of ligand-bound AR; JMJD2C, and LSD1 into a multiple-specificity demethylase complex.

Figure 2B:
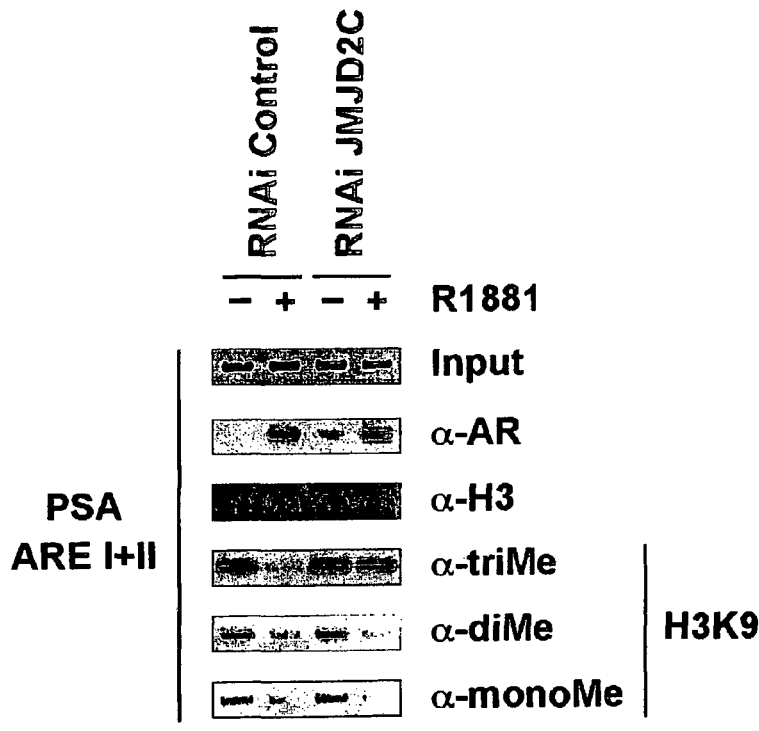
Figure 2B:
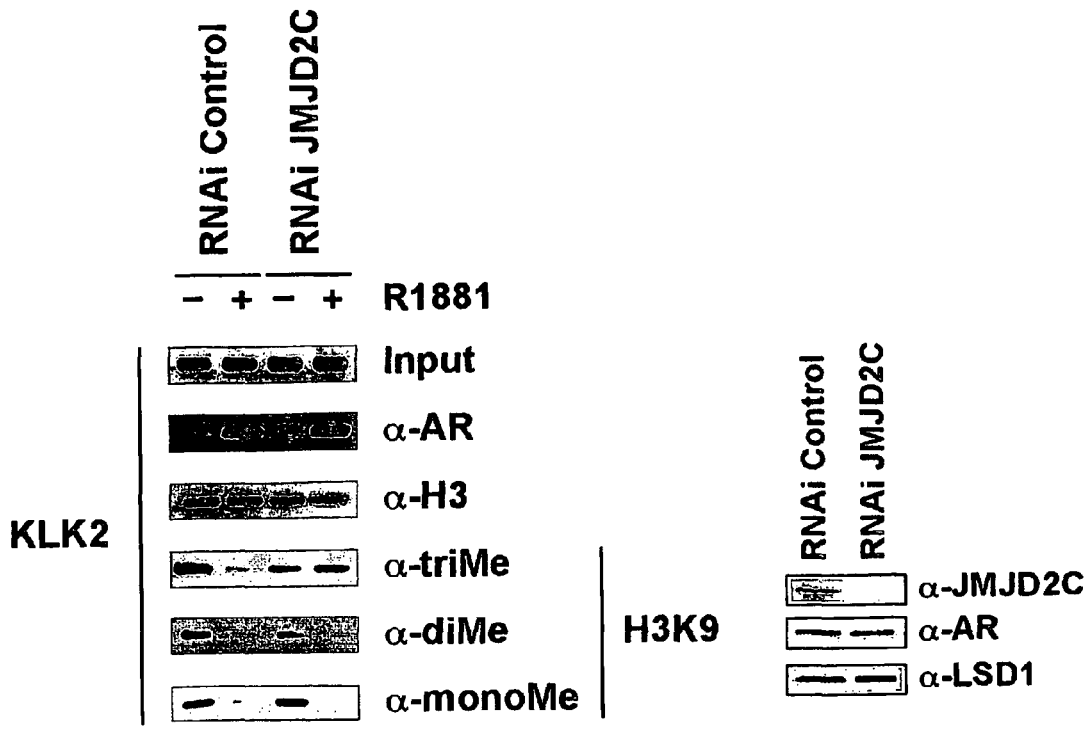
Figure 2:
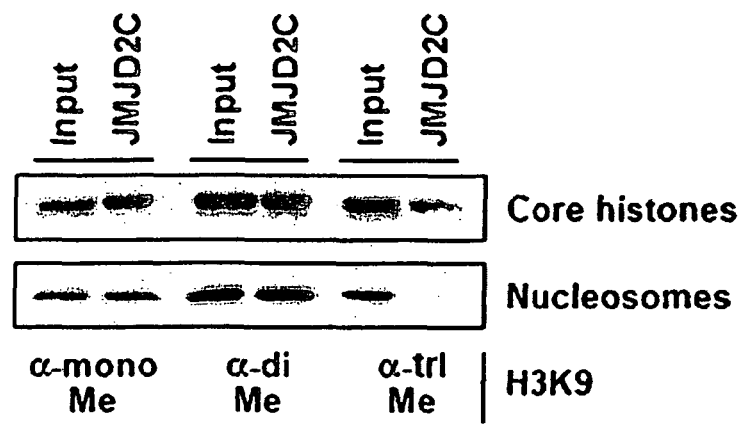
Figure 2:
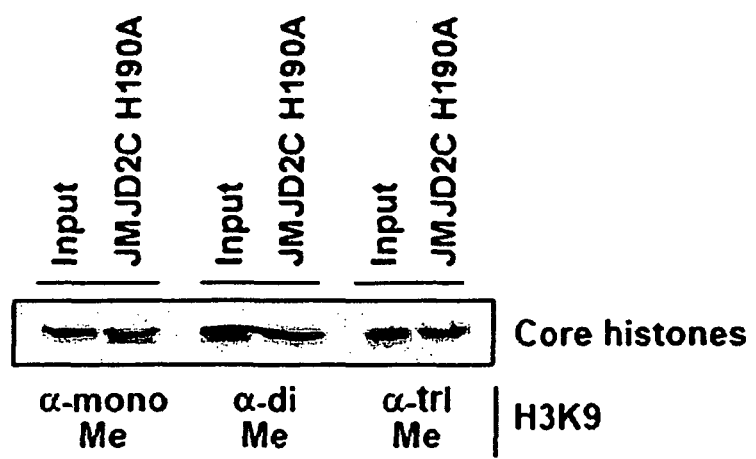

Since androgen-stimulated transcription is accompanied by a robust decrease in mono-, di-, and trimethyl H3K9 at the PSA promoter[3], we tested whether JMJD2C executes the ligand-dependent demethylation of trimethyl H3K9. Transfection of LNCaP cells with siRNAs directed against JMJD2C blocks efficiently ligand-dependent demethylation of trimethyl. H3K9 at the PSA promoter but not that of mono- and dimethyl H3K9 (FIG. 2b). JMJD2C knockdown is specific and does neither affect the level of endogenous AR and LSD1 nor the protein levels of the other JMJD2 family members (FIG. 2b). Furthermore, the amount of total H3 on the PSA promoter is not influenced by JMJD2C knockdown and the methylation status of H3K9 is not altered by an unrelated control siRNA (FIG. 2b). Similar results were obtained with the AR-regulated[15] Kallikrein (KLK2) promoter (FIG. 2b). To further validate that JMJD2C specifically removes trimethyl H3K9 marks, we performed demethylation assays in, vitro. Recombinantly expressed and purified JMJD2C was, incubated with either core histones or HeLa nucleosomes as substrates (FIG. 2c; FIG. 6). Recombinant JMJD2C very efficiently demethylates trimethyl H3K9 on both core histones and nucleosomes in vitro, whereas the methylation status of mono- and dimethyl H3K9 is not altered, corroborating demethylation results obtained with trimethyl H3K9 peptide as a substrate[5,6]. As expected, the enzymatically impaired mutant JMJD2C H190A[5] fails to demethylate (FIG. 2c; FIG. 6). Taken together, these data show the specific demethylation of the repressive histone mark trimethyl H3K9 by JMJD2C.

Next, we performed transient transfection assays to test whether JMJD2C modulates the transcriptional activity of AR. Co-expression of AR and increasing amounts of JMJD2C results in a strong ligand-dependent activation of a PSA luciferase reporter, which is not observed in the absence of either ligand or of AR (FIG. 7a). In addition, other members of the JMJD2 family do not influence the transcriptional activity of AR (FIG. 3a). Interestingly, JMJD2C activates also other members of the nuclear receptor superfamily such as glucocorticoid receptor (GR) and progesterone receptor (PR), but not thyroid receptor α (TRα), estrogen receptor α (ERα), or vitamin D receptor (VDR). Stimulation of AR activity by JMJD2C is potent in different cell lines, and various. AR-responsive promoters are activated by JMJD2C in a ligand-dependent manner (FIG. 3b-d). The fact that JMJD2C and LSD1 are co-expressed in prostate cells and assemble in a complex on the PSA promoter in vivo suggested a functional co-operativity of these two demethylases. To address this issue we tested limited amounts of LSD1 or JMJD2C, which alone only weakly stimulate ligand-dependent AR activity (FIG. 3e). Importantly, co-expression of limited amounts of both demethylases induces robust co-operative stimulation of AR (FIG. 3e). In contrast, co-expression of LSD1 and the mutant JMJD2C H190A results in a weak superactivation of AR (FIG. 3e). Taken together, these data show that demethylases with different substrate specificities co-operate to stimulate AR-dependent gene expression.

Since removal of the repressive histone, mark trimethyl H3K9 by JMJD2C increases. AR-dependent gene expression, knockdown of JMJD2C should reduce the expression of endogenous AR target genes. In order to test this hypothesis we infected LNCaP cells with lentiviruses expressing miRNA directed against JMJD2C. This results in efficient and specific down-regulation of endogenous JMJD2C (FIG. 4a). Quantitative RT-PCR analyses demonstrate that knockdown of JMJD2C blocks androgen-induced expression of endogenous AR target genes such as PSA or KLK2 in LNCaP cells (FIG. 4a; FIG. 7b). Similarly, vector-mediated JMJD2C knockdown by the same miRNAs results in a strong ligand-dependent decrease of MMTV-LUC reporter gene expression (FIG. 4b). To address whether JMJD2C governs androgen-dependent cell growth, we analysed proliferation of pLenti6-miRNA-JMJD2C-infected LNCaP cells. Importantly, when compared to cells infected with the virus expressing an unrelated control miRNA, androgen-induced proliferation of LNCaP cells is dramatically reduced by JMJD2C knockdown (FIG. 4c). These results demonstrate the importance of JMJD2C in the control of androgen-induced gene regulation and cell proliferation.

Taken together, our data show that the trimethyl-specific histone demethylase JMJD2C controls AR function. JMJD2C and ligand-bound AR associate at androgen-regulated promoters, which results in specific demethylation of the repressive histone mark trimethyl H3K9. Importantly, we unravel a novel mechanism by which the co-operative action of the two demethylases JMJD2C and LSD1 leads to removal of the repressive mono-, di-, and trimethyl marks on H3K9. Thus, the action of a multiple demethylation complex with distinct substrate specificities allows the optimal activation of AR target genes. Notably, both JMJD2C and LSD1 are co-expressed with AR in human prostate tumours, and reduction of either LSD1[3] or JMJD2C severely inhibits androgen-dependent proliferation of prostate tumour cells. Thus, specific modulation of JMJD2C activity alone or in combination with LSD1 might be a promising therapeutic strategy to control AR activity in tissues where AR plays a pivotal physiological role.

Methods

Plasmids

The following plasmids were described previously: pSG5-AR, CMX-Flag, GST-AR-NTD, GST-AR-DBD, GST-AR-LBD, PR, GR, VDR, MMTV-LUC, $Spp_{2x}$-TK-LUC, Probasin-LUC, and PSA-LUC[16]; GST-LSD1, GST-LSD1-NTD, GST-LSD1-SWIRM, GST-LSD1-AO, GST-Nix1, ERα, TREp-LUC, and $ERE_{2x}$-TATA-LUC, TAP, TAP-LSD1, and Flag-AR[3]; pJAL-JMJD2A[17]. To construct CMX-Flag-JMJD2C, CMX-Flag-JMJD2C H190A, CMX-Flag-JMJD2D, CMX-DEST51-JMJD2B, CMX-DEST51-JMJD2C, pRSET-JMJD2C (aa12-349), and pRSET-JMJD2C H190A (aa12-349), the corresponding fragments were inserted into pCMX-Flag, pCMX-DEST51, pGEX4T-1, or pRSET. To construct pLenti6-miRNA1-JMJD2C, pLenti6-miRNA2-JMJD2C, pGW-miRNA1-JMJD2C, and pGW-miRNA2-JMJD2C, the DNA corresponding to miRNA1-JMJD2C (5'-TGCTGAAATGCATCACACCCTTGGG-AGTTTTGGCCACTGACTGACTC-CCAAGGGTGATGCATTT-3' (SEQ ID NO: 7) and 5'-CCT-GAAATGCATCACCCTTGGGAGTCAGT-CAGTGGCCAAAACTCCCAAGGGTGTGATGCATTC-3' (SEQ ID NO: 81) and miRNA2-JMJD2C (5'-TGCTGT-TAAGCAGCTGTTTCCTGAGAGTTTTGGC-CACTGACTGACTCTCAGGACAGCTGCTTAA-3' (SEQ ID NO: 9) and 5'-CCTGTTAAGCAGCTGCTGTCCT-GAGAGTCAGTCAGTGGCCAAAACTCT-CAGGAAACAGCTGCTTAAC-3' (SEQ ID NO: 10)) was cloned into pLenti6N5-DEST and pcDNA-6.2-GW-EmGFP according to the manufacturer's instruction (Invitrogen). Cloning details can be obtained upon request.

Cell Culture and Transfection

CV1 and LNCaP cells were cultured and transfected as described[18]. The following amounts were transfected per well 500 ng of MMTV-LUC, PSA-LUC, Probasin-LUC, TREp-LUC, $ERE_{2x}$-TATA-LUC, or $Spp_{2x}$-TK-LUC; 25 ng of AR, PR, GR, TR☐, ERα, or VDR expression plasmid; 200 ng (FIG. 3e) or 400 ng (FIG. 3a-d) expression plasmids of LSD1, JMJD2A/B/C/D, or JMJD2C H190A, 1000 ng expression plasmid of miRNA-control, miRNA1-JMJD2C, or miRNA2-JMJD2C. Cells were treated in the presence or absence of $10^{-10}$ M R1881, $10^{-7}$ M R5020, $10^{-7}$ M dexamethasone (Dex), $10^{-7}$ M estradiol (E2), $10^{-7}$ M thyroid hormone (T3), $10^{-7}$ M vitamin D (Vit D) (Sigma) for 18 hours as indicated. Luciferase activity was assayed as described[18]. All experiments were repeated at least five times in duplicate.

Immunohistochemistry

Polyclonal rabbit α-JMJD2C antibody was generated according to standard procedures. Stainings were performed using a protocol[19] for antigen retrieval and indirect immunoperoxidase. α-AR 441 (Santa Cruz), α-LSD1[3], and α-JMJD2C antibodies were used at a dilution of 1:75, 1:500, and 1:50, respectively. Rabbit and mouse IgG were used as secondary antibodies (1:500; Dako). Immunoreactions were visualised with the ABC-complex diluted 1:50 in PBS (Vectastain, Vector).

Chromatin Immunoprecipitation

ChIP experiments were performed as described[3]. LNCaP cells were treated for 45 min (FIG. 2a) or 210 min in the presence or absence of $10^{-8}$ M R1881 as indicated. LNCaP cells were transfected three days before harvesting for ChIP with or without stealth RNAi (Invitrogen) following the manufacturer's instructions. Immunoprecipitation was performed with specific antibodies (α-monoMeH3K9, α-diMeH3K9, α-triMeH3K9, α-H3, α-AR PG21 (Upstate Biotechnology), α-LSD1[3], and α-JMJD2C) on GammaBind™-Sepharose 4B (GE-Healthcare). For PCR, 1-5 µl out of 50 d DNA extract was used. For Re-ChIP assays, immunoprecipitations were sequentially washed with TSE I, TSE II, buffer III, and TE[20]. Complexes were eluted by incubation with 10 mM DTT at 37° C. for 30 minutes, diluted 50 times with dilution buffer[20] followed by a second immunoprecipitation with the indicated antibodies. PCR primers for ARE I+II (PSA -459/-121), ARE III (PSA -4288/-3922), GAPDH, and U6 were described previously[3]. Primer sequences for the promoter region (-343/-90) of the KLK2 gene are as follows:

(5'-ACCCCTGTTGCTGTTCATCCTG-3'
(SEQ ID NO: 11)
and

5'-CCGCCCTTGCCCTGTTGG-3').
(SEQ ID NO: 12)

Co-Immunoprecipitation Assay and Western Blot Analysis

Experiments were performed as described[16]. Immunoprecipitations from extracts of murine prostate were performed in the presence of $10^{-10}$ M R1881 with either α-JMJD2C, α-LSD1[3], α-cyclin A[19] antibodies, or rabbit IgG. Western blots were decorated as indicated including α-AR antibody (N-20, Santa Cruz). 1.5 percent of prostate extract used for the co-immunoprecipitation was loaded as input.

In Vitro Pull-Down Assay

GST pull-down assays were performed with equal amounts of GST or GST fusion proteins as described[19] using buffer containing 150 mM KCl and 0.15% NP-40. Ten percent of the in vitro translated proteins used for the pull-down were loaded as input.

Cell Proliferation Assay

Experiments were performed as described[3]. pLenti6-miRNA-control and pLenti6-miRNA1-JMJD2C were used to produce recombinant lentiviruses to infect LNCaP cells as described[21]. The infected cells were cultured for 72 hours in medium containing 10% double-stripped FCS. $1 \times 10^4$ cells were plated in a 96-well plate in the presence or absence of $10^{-9}$ M R1881. The cell proliferation Elisa BrdU Colorimetric Assay (Roche) was performed according to the manufacturer's instructions. The figure shows the percentage increase of proliferation in the presence versus absence of R1881. The experiment was performed in quintuplicate.

Quantitative RT-PCR and Statistical Analysis

Quantitative RT-PCR and statistical analysis were done as described[3]. The primers for GAPDH and PSA were described previously[3].

In Vitro Demethylation Assay

The demethylation assays were performed as described[4]. His-tagged proteins were incubated for 5 hours at 37° C. in demethylation buffer containing 50 mM HEPES-KOH pH 8.0, 2 mM ascorbate, 100 µM $Fe(NH_4)_2(SO_4)_2$, 1 mM α-ketoglutarate with 1 µg of nucleosomes or core histones purified from HeLa cells[22]. The reaction mixture was analysed by SDS-PAGE followed by Western blotting using antibodies as indicated.

Tandem Affinity Purification

TAP purification was essentially performed as described[23]. Nuclear extracts from 293 cells transfected with Flag-AR, V5-JMJD2C, and either TAP-tag-LSD1 (TAP-LSD1) or control TAP-tag (TAP) were prepared in SC buffer (50 mM TrisHCl pH 8, 170 mM NaCl, 20% Glycerol, 0.2 mM DTT, 0.1% NP-40, R1881 $10^{-9}$ M, 50 mM NaF, 2 mM $Na_3VO_4$, and Complete® protease inhibitor cocktail). TAP-tagged proteins were bound to IgG-sepharose (GE-Healthcare) in SC buffer at 4° C. over night followed by repeated washing. Bound complexes were released from IgG-sepharose by TEV-protease cleavage (100 U, Invitrogen) in TEV buffer (10 mM TrisHCl pH 8.0, 150 mM NaCl, 0.1% NP40, 1 mM DTT, 1 mM EDTA, R1881 $10^{-9}$ M). Immunoprecipitation was performed with or α-Flag antibody.

LITERATURE

1. Strahl, B. D. & Allis, C. D. The language of covalent histone modifications. *Nature* 403, 41-45. (2000).
2. Shi, Y. et al. Histone demethylation mediated by the nuclear amine oxidase homolog LSD1. *Cell* 119, 941-953. (2004).
3. Metzger, E. et al. LSD1 demethylates repressive histone marks to promote androgen-receptor-dependent transcription. *Nature* 437, 436-439. (2005).
4. Tsukada, Y. I. et al. Histone demethylation by a family of JmjC domain-containing proteins. *Nature* 435, 811-816. (2005).
5. Whetstine, J. R. et al. Reversal of Histone Lysine Trimethylation by the JMJD2 Family of Histone Demethylases. *Cell* 125, 467-481. (2006).
6. Cloos, P. A. et al. The putative oncogene GASC1 demethylates tri- and dimethylated lysine 9 on histone H3. *Nature* 442, 307-311. (2006).

7. Shi, X. et al. ING2 PHD domain links histone H3 lysine 4 methylation to active gene repression. *Nature* 442, 96-99. (2006).
8. Wysocka, J. et al. A PHD finger of NURF couples histone H3 lysine 4 trimethylation with chromatin remodelling. *Nature* 442, 86-90. (2006).
9. Rosenfeld, M. G., Lunyak, V. V. & Glass, C. K. Sensors and signals: a coactivator/corepressor/epigenetic code for integrating signal-dependent programs of transcriptional response. *Genes Dev.* 20, 1405-1428. (2006).
10. Yamane, K. et al. JHDM2A, a JmjC-Containing H3K9 Demethylase, Facilitates Transcription Activation by Androgen Receptor. *Cell* 125, 483-495. (2006).
11. Trewick, S. C., McLaughlin, P. J. & Allshire, R. C. Methylation: lost in hydroxylation? *EMBO Rep.* 6, 315-320. (2005).
12. Fodor, B. D. et al. Jmjd2b antagonizes H3K9 trimethylation at pericentric heterochromatin in mammalian cells. *Genes Dev.* 20, 1557-1562. (2006).
13. Klose, R. J. et al. The transcriptional repressor JHDM3A demethylates trimethyl histone H3 lysine 9 and lysine 36. *Nature* 442, 312-316. (2006).
14. Trojer, P. & Reinberg, D. Histone lysine demethylases and their impact on epigenetics. *Cell* 125, 213-217. (2006).
15. Kang, Z., Pirskanen, A., Janne, O. A. & Palvimo, J. J. Involvement of proteasome in the dynamic assembly of the androgen receptor transcription complex. *J. Biol. Chem.* 277, 48366-48371. (2002).
16. Metzger, E., Müller, J. M., Ferrari, S., Buettner, R. & Schüle, R. A novel inducible transactivation domain in the androgen receptor: implications for PRK in prostate cancer. *EMBO J.* 22, 270-280. (2003).
17. Gray, S. G. et al. Functional characterization of JMJD2A, a histone deacetylase- and retinoblastoma-binding protein. *J. Biol. Chem.* 280, 28507-28518. (2005).
18. Müller, J. M. et al. The transcriptional coactivator FHL2 transmits Rho signals from the cell membrane into the nucleus. *EMBO J.* 21, 736-748. (2002).
19. Müller, J. M. et al. FHL2, a novel tissue-specific coactivator of the androgen receptor. *EMBO J.* 19, 359-369. (2000).
20. Shang, Y., Myers, M. & Brown, M. Formation of the androgen receptor transcription complex. *Mol. Cell.* 9, 601-610. (2002).
21. Wiznerowicz, M. & Trono, D. Conditional suppression of cellular genes: lentivirus vector-mediated drug-inducible RNA interference. *J. Virol.* 77, 8957-8961. (2003).
22. O'Neill, T. E., Roberge, M. & Bradbury, E. M. Nucleosome arrays inhibit both initiation and elongation of transcripts by bacteriophage T7 RNA polymerase. *J. Mol. Biol.* 223, 67-78. (1992).
23. Rigaut, G. et al. A generic protein purification method for protein complex characterization and proteome exploration. *Nat. Biotechnol.* 17, 1030-1032. (1999).
24. Busso, D., Delagoutte-Busso, B. & Moras, D. Construction of a set Gateway-based destination vectors for high-throughput cloning and expression screening in *Escherichia coli*. *Anal. Bioch.* 343, 313-321. (2005).

The invention claimed is:

1. A process for searching for and/or screening substances controlling the interaction of lysine-specific demethylase 1 (LSD1) and Jumonji C domain containing protein (JMJD2C), said process comprising the steps of: contacting at least one substance to be searched for or to be screened with a reaction system comprising a complex of LSD1 and JMJD2C, and at least one compound capable of being demethylated enzymatically on mono-, di- and tri-methyl lysine residues by said complex and evaluating the influence of said at least one substance to be searched for or screened on the enzymatic demethylation on said mono-, di- and tri-methyl lysine residues, wherein said compound comprises mono-, di- and tri-methyl lysine residues.

2. The process according to claim 1, wherein said substances modulate the demethylase activity of LSD1 and JMJD2C.

3. The process according to claim 1, wherein the compound capable of being demethylated enzymatically is an androgen response element (ARE) and wherein said at least one substance controls the modulating activity of LSD1 and JMJD2C on the ARE.

* * * * *

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial
<220> FEATURE:
<223> OTHER INFORMATION: Synthesized: Primer, ARE I, forward

<400> SEQUENCE: 1
tttgtcccct agatgaagtc tcc                                            23

<210> SEQ ID NO 2
<211> LENGTH: 23
<212> TYPE: DNA
<213> ORGANISM: Artificial
<220> FEATURE:
<223> OTHER INFORMATION: Synthesized: Primer, ARE I, reverse

<400> SEQUENCE: 2
cccacaccca gagctgtgga agg                                            23

<210> SEQ ID NO 3
<211> LENGTH: 23
<212> TYPE: DNA
<213> ORGANISM: Artificial
<220> FEATURE:
<223> OTHER INFORMATION: Synthesized: Primer, ARE II, forward

<400> SEQUENCE: 3
gccaagacat ctatttcagg agc                                            23

<210> SEQ ID NO 4
<211> LENGTH: 22
```

-continued

```
<212> TYPE: DNA
<213> ORGANISM: Artificial
<220> FEATURE:
<223> OTHER INFORMATION: Synthesized: Primer, ARE II, reverse

<400> SEQUENCE: 4
cctttgcact ccaagaccca gt                                         22

<210> SEQ ID NO 5
<211> LENGTH: 23
<212> TYPE: DNA
<213> ORGANISM: Artificial
<220> FEATURE:
<223> OTHER INFORMATION: Synthesized: Primer, ARE III, forward

<400> SEQUENCE: 5
tgctcagcct ttgtctctga tga                                        23

<210> SEQ ID NO 6
<211> LENGTH: 23
<212> TYPE: DNA
<213> ORGANISM: Artificial
<220> FEATURE:
<223> OTHER INFORMATION: Synthesized: Primer, ARE III, reverse

<400> SEQUENCE: 6
atatctctct cagatccagg ctt                                        23

<210> SEQ ID NO 7
<211> LENGTH: 64
<212> TYPE: DNA
<213> ORGANISM: Artificial
<220> FEATURE:
<223> OTHER INFORMATION: Synthesized: Insert; miRNA1-JMJD2C, forward

<400> SEQUENCE: 7
tgctgaaatg catcacaccc ttgggagttt tggccactga ctgactccca agggtgatgc 60
attt                                                             64

<210> SEQ ID NO 8
<211> LENGTH: 63
<212> TYPE: DNA
<213> ORGANISM: Artificial
<220> FEATURE:
<223> OTHER INFORMATION: Synthesized: Insert; miRNA1-JMJD2C; reverse

<400> SEQUENCE: 8
cctgaaatgc atcacccttg ggagtcagtc agtggccaaa actcccaagg gtgtgatgca 60
ttc                                                              63

<210> SEQ ID NO 9
<211> LENGTH: 64
<212> TYPE: DNA
<213> ORGANISM: Artificial
<220> FEATURE:
<223> OTHER INFORMATION: Synthesized: Insert; miRNA2-JMJD2C; forward

<400> SEQUENCE: 9
tgctgttaag cagctgtttc ctgagagttt tggccactga ctgactctca ggacagctgc 60
ttaa                                                             64

<210> SEQ ID NO 10
<211> LENGTH: 67
<212> TYPE: DNA
<213> ORGANISM: Artificial
```

```
<220> FEATURE:
<223> OTHER INFORMATION: Synthesized: Insert; miRNA2-JMJD2C; reverse

<400> SEQUENCE: 10
cctgttaagc agctgctgtc ctgagagtca gtcagtggcc aaaactctca ggaaacagct    60
gcttaac                                                              67

<210> SEQ ID NO 11
<211> LENGTH: 22
<212> TYPE: DNA
<213> ORGANISM: Artificial
<220> FEATURE:
<223> OTHER INFORMATION: Synthesized: Primer; KLK2 gene; forward

<400> SEQUENCE: 11
acccctgttg ctgttcatcc tg                                             22

<210> SEQ ID NO 12
<211> LENGTH: 18
<212> TYPE: DNA
<213> ORGANISM: Artificial
<220> FEATURE:
<223> OTHER INFORMATION: Synthesized: Primer; KLK2 gene; reverse

<400> SEQUENCE: 12
ccgcccttgc cctgttgg                                                  18
```